United States Patent [19]

Green et al.

[11] Patent Number: 4,970,397
[45] Date of Patent: Nov. 13, 1990

[54] METHOD AND APPARATUS FOR ACTIVATING CATALYSTS USING ELECTROMAGNETIC RADIATION

[75] Inventors: Gary J. Green, Yardley, Pa.; Stuart D. Hellring, Houston, Tex.

[73] Assignee: Mobil Oil Corp., Fairfax, Va.

[21] Appl. No.: 367,175

[22] Filed: Jun. 16, 1989

[51] Int. Cl.$^5$ .......................... G01J 3/42; G01J 37/38
[52] U.S. Cl. .................................. 250/341; 502/522; 250/343
[58] Field of Search ............... 250/341, 340, 343, 352, 250/338.1; 502/60, 522; 356/36

[56] References Cited

U.S. PATENT DOCUMENTS

| | | |
|---|---|---|
| Re. 29,948 | 3/1979 | Dwyer et al. |
| 3,702,886 | 11/1972 | Argauer et al. |
| 3,709,979 | 1/1973 | Chu . |
| 3,832,449 | 8/1974 | Rosinski et al. |
| 3,856,872 | 12/1974 | Morrison . |
| 4,016,218 | 4/1977 | Haag et al. |
| 4,016,245 | 4/1977 | Plank et al. |
| 4,046,859 | 9/1977 | Plank et al. |
| 4,086,186 | 4/1978 | Rubin et al. |
| 4,100,262 | 7/1978 | Pelrine . |
| 4,107,195 | 8/1978 | Rollmann .. |
| 4,139,600 | 2/1979 | Rollmann et al. |
| 4,551,437 | 11/1985 | Benebi ................................. 502/522 |
| 4,559,314 | 12/1985 | Shihabi . |
| 4,696,732 | 9/1987 | Angevine et al. |

OTHER PUBLICATIONS

S. H. Moon et al., A Simple-Design High Vacuum Infrared Cell for In-Situ Studies of Supported Metal Catalysts, Ind. Eng. Chem. Fundam., 20, pp. 396-399 (1981).

A. D. Abbate et al., Activation and Cleaning of Oxide Surfaces by a CW $CO_2$ Laser, Surface Science 136, L19-L24 (1984).

O'Shea, An Introduction to Lasers and Their Applications, pp. 94-97, Addison-Wesley (1977).

Yariv, Introduction to Optical Electronics, pp. 39-43, Rinehart & Winston (1976).

Primary Examiner—Janice A. Howell
Assistant Examiner—Richard Hanig
Attorney, Agent, or Firm—Alexander J. McKillop; Charles J. Speciale; Dennis P. Santini

[57] ABSTRACT

This invention relates to electromagnetically induced thermal activation method and apparatus for in-situ preparation of samples including zeolite catalyst. More particularly, the invention relates to preparation of samples for IR spectroscopic characterization analysis. The technique is based on electromagnetically introduced thermal treatment of a catalyst situated in a specially designed vacuum cell which is housed in the sample compartment of an IR analyzer. The sample is selectively heated by adsorption of direct infrared radiation from a laser. The sample is supported on a negligible mass which preferably comprises a wire made of nichrome.

54 Claims, 3 Drawing Sheets

ZSM-5: BEFORE DESORPTION

ZSM-5: FULLY DESORBED BY EITD 2W, 30 SEC

ZSM-5: FULLY DESORBED USING THERMAL CELL 450°C, 1 HOUR HOLD

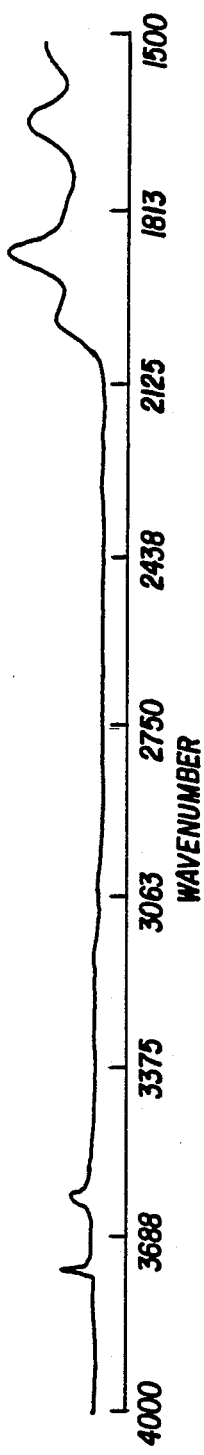
FIG. 3(a) ZSM-5: DEHYDROXYLATION BY EITD 4W, 30 SEC.
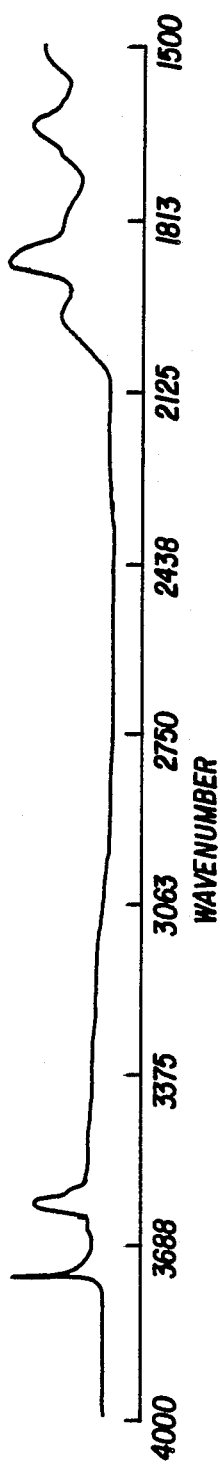
FIG. 3(b) ZSM-5: FULLY DESORBED BY EITD 2W, 30 SEC.

METHOD AND APPARATUS FOR ACTIVATING CATALYSTS USING ELECTROMAGNETIC RADIATION

FIELD OF THE INVENTION

This invention relates to activating samples, in particular, zeolite type catalysts, using a beam of electromagnetic radiation having a wavelength between about 0.1 $\mu$m and 100 $\mu$m.

BACKGROUND OF THE INVENTION

Desorption of adsorbed water and other impurities from oxides can be accomplished by conventional, resistively heated thermal cells. A detailed explanation of a conventional thermal cell is taught by S. H. Moon et al., *A SIMPLE-DESIGN HIGH VACUUM INFRARED CELL FOR IN-SITU STUDIES OF SUPPORTED METAL CATALYSTS*, Ind. Eng. Chem. Fundam., 20, 396-399 (1981), hereby incorporated by reference. The article reports a vacuum IR cell. The cell uses commercial vacuum adaptors containing O-ring seals, that degrade at high temperature, as the IR window holders. The adaptors may be disassembled easily for sample introduction into the cell. The device is cooled to prevent degradation of the seals. The cell was operated continuously and periodically at 550° C. without use of a beam of electromagnetic radiation. A basic design for the cell is presented.

The IR cell consists of several main parts. The center part is a quartz tube of 1 in. O.D. and ⅞ in. I.D. and has a ¼ in. quartz tube and a high vacuum stopcock near each end to permit gas introduction or flow. A sample holder is positioned in the center of the tube so that a catalyst wafer is located at the center of the cell. The center unit is wrapped with heating wire and insulation for high temperature operation of the cell and sample. Temperature is measured by a thermocouple positioned directly behind the sample holder. The holder is made of quartz tube having an O.D. about ⅞ in. Two annular quartz plates with ⅜ in. center holes are attached to one end of the sample holder. The plates are spaced to position the catalyst wafer between them perpendicular to the IR beam. The ends of the cell are sealed by IR windows constructed of NaCl.

Activation and cleaning of oxide surfaces using electromagnetic radiation has been taught by A. D. Abbate et al., *ACTIVATION AND CLEANING OF OXIDE SURFACES BY A CW CO₂ LASER*, Surface Science 136, L19-L24 (1984), hereby incorporated by reference. This article teaches that electromagnetic radiation heating is a generally useful tool for the cleaning and activation of portions of oxide surfaces. Such surfaces can be used as catalysts. The oxide surface itself is heated. The technique is particularly suitable for samples which have a small thermal conductivity. According to the article, oxide samples were pressed into two centimeter diameter disks which were sandwiched between copper washers with an 11 millimeter aperture. A stainless steel flange pressed the sandwich against the recessed ledge in a copper block. It was resistively heated to 250° C. or cooled with liquid nitrogen. The assembly was enclosed in a vacuum stainless steel cell. According to the article, laser heating has been shown to accelerate the dehydroxylation of silica disks. The article reports physical removal of adsorbed water and hydrogen bonded hydroxyls on silica, $Al_2O_3$ and zinc oxide surfaces. These are not zeolites which have distinct three dimentional crystalline structures. The reference indicated that the radical intensity distribution was not Gaussian, that is, not $TEM_{oo}$. Samples were prepared by laser heating alone or with simultaneous heating of the sample holder. Notwithstanding this, all the samples treated in this reference were prepared by resistively heating the cell to 140° C., in addition to laser heating. Irradiation times were 10 to 30 min. The reference further indicated that heating uniformity would be improved with better control of the laser modes.

The prior art teaches electromagnetic irradiation utilizing awkward procedures and apparatus. The prior devices necessitate heating the cell as well as the sample. The devices require substantial disassembly for sample manipulation. Applicants have overcome disadvantages through their inventive process and apparatus for selectively activating the entire sample by laser heating just the sample for a very brief time period.

SUMMARY OF THE INVENTION

This invention relates to a method for selectively thermally treating samples comprising essentially instantaneously activating a sample exclusively using a beam of electromagnetic radiation having a wavelength between about 0.1 $\mu$m and 100 $\mu$m and an energy distribution given by transverse electromagnetic mode $TEM_{oo}$ and analyzing the selectively thermally treated sample.

This invention also relates to a cell for thermally activating and analyzing samples comprising a sample holder having a substantially negligible mass to support a sample, the cell is constructed and arranged so that a beam of electromagnetic radiation means exclusively heats the sample supported by the sample holder and so that the irradiated sample can also be analyzed essentially simultaneously.

This invention further relates to a cell for thermally activating and analyzing samples comprising at least three conduits, two of the conduits having longitudinal axes which intersect in one plane, the third conduit having a longitudinal axis which intersects the intersection of the axes of the two conduits, these two conduits being sealed at their distal end by laser and analyzer visible windows, a rotatable sample holder comprising a fine wire holder is located in the cell, the sample holder has a longitudinal axis parallel to that of the third conduit, the distal ends of the third conduit are sealed.

This invention also relates to an apparatus for thermally activating and analyzing samples comprising a source for a beam of electromagnetic radiation, a variable polarization analyzer, beam splitter, and beam expander for processing the electromagnetic radiation which then irradiates a sample supported in a cell sealed in an enclosure which cell is constructed and arranged so that the electromagnetic radiation exclusively heats the sample supported by a sample holder in the cell and so that the irradiated sample can also be analyzed essentially simultaneously.

BRIEF DESCRIPTION OF THE DRAWINGS

Without limiting the scope of this invention, it will now be described with respect to the drawings.

FIG. 3 depicts the results of experimentation upon a ZSM-5 zeolite type catalyst and shows the effects of dehydroxylation and desorption;

DETAILED DESCRIPTION OF THE INVENTION

Figure 1:
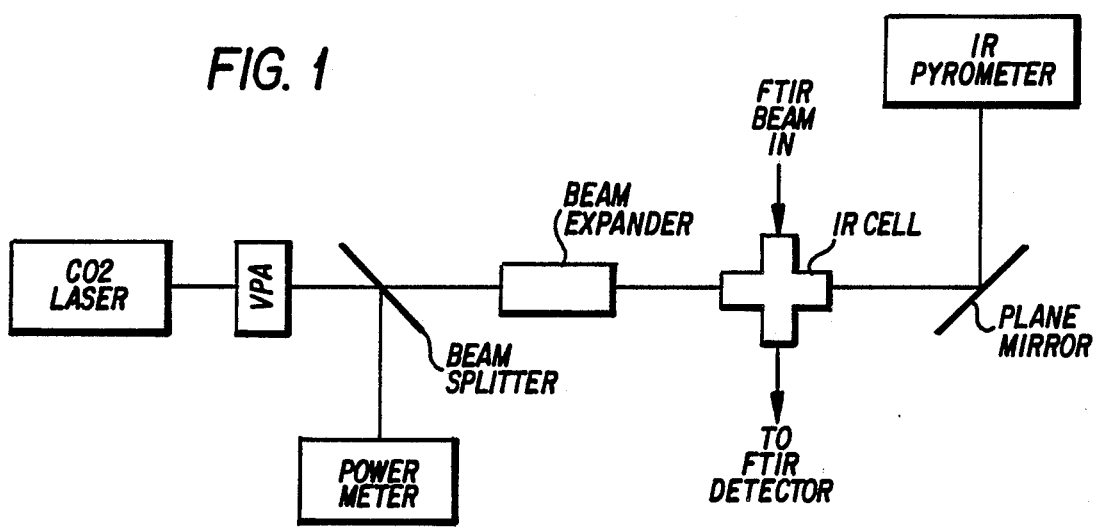
FIG. 1 depicts a schematic representation of the process and apparatus of the present invention.

The invention relates to a novel integrated apparatus for in-situ preparation of catalyst samples for FTIR spectroscopic characterization. The technique is based on electromagnetic radiation induced thermal treatment of a catalyst situated in a specially designed vacuum cell. The cell is housed in the sample compartment of a commercial FTIR. The catalyst sample is selectively heated by absorption of directed infrared radiation from a laser; no other parts of the cell are heated. The method is especially useful when applied to zeolite samples which must be desorbed of $H_2O$, hydrocarbons, etc. to insure accurate quantitative measurements of acidic -OH (framework Al) concentration. The technique is also capable of in-situ dealumination of zeolites to modify catalytic activity, which is another example of activation in addition to desorption, dehydroxylation, and phase transition just to mention some exemplary kinds of physico-chemical transformation of the sample.

This approach provides a simple and effective alternative to conventional prior art thermal cells, such as those mentioned above, which have been used for $H_2O$ desorption from zeolites. Sample throughput (number of samples analyzed/time) is extremely low due to long heat-up and cool-down times associated with a resistively heated furnace block and sample holder according to the prior art processes and devices. Typical time required to characterize one sample using a conventional cell is about 4 to 5 hours. Because only the catalyst sample is heated, applicants' design reduces this to about 0.5 to 3 minutes by eliminating the heat-up and cool-down of a furnace block and sample holder. Treatment analysis, unloading the sample and reloading a new sample is typically complete in less than 15 minutes. Complications such as leakage of seals or breakage of IR windows are also eliminated with applicants' cell.

Another object of the invention is to provide for much higher temperature treatment of catalyst samples than has been possible using prior art thermal cells. Sample temperatures exceeding 1000° C. can be achieved in the FTIR vacuum cell by use of the present laser technique. The rapid, routine in-situ preparation of FTIR characterization of dealuminated (dehydroxylated) zeolites in vacuum is now possible.

Additional objects of the invention are to permit rapid sample repositioning from thermal treatment to spectroscopic analysis within the cell and to allow quick removal and insertion of new samples. The novel design of the rotary, low mass sample holder accomplishes these objects as described more fully below.

The kinds of samples that can be treated here are those which are selectively heated by a laser having a wavelength between about 0.1 $\mu$m and 100 $\mu$m and an energy distribution given by transverse electromagnetic mode $TEM_{oo}$. Examples of samples are zeolite catalysts, etc.

A convenient measure of the extent to which a zeolite provides control to molecules of varying sizes to its internal structure is the Constraint Index of the zeolite. The method by which the Constraint Index is determined is described in U.S. Pat. No. 4,016,218, incorporated herein by reference for details of the method. U.S. Pat. No. 4,696,732 discloses Constraint Index values for typical zeolite materials and is incorporated by reference as if set forth at length herein.

In a preferred embodiment, the catalyst is a zeolite having a Constraint Index of between about 1 and about 12. Examples of such zeolite catalysts include ZSM-5, ZSM-11, ZSM-12, ZSM-34, ZSM-35, ZSM-38, alpha zeolite, APO zeolite or layered silicate.

Zeolite ZSM-5 and the conventional preparation thereof are described in U.S. Pat. No. 3,702,886. Other preparations for ZSM-5 are described in U.S. Patent Nos. Re. 29,948 (highly siliceous ZSM-5); 4,100,262 and 4,139,600. Zeolite ZSM-11 and the conventional preparation thereof are described in U.S. Pat. No. 3,709,979. Zeolite ZSM-12 and the environmental preparation thereof are described in U.S. Pat. No. 3,832,449. Zeolite ZSM-34 and the conventional preparation thereof are described in U.S. Pat. No. 4,086,186. Zeolite ZSM-35 and the conventional preparation thereof are described in U S. Pat. No. 4,016,245. Another preparation of ZSM-35 is described in U.S. Pat. No. 4,107,195. ZSM-38 and the conventional preparation thereof is taught by U.S. Pat. No. 4,046,859. The preceding references are incorporated herein by reference.

Catalysts such as ZSM-5 combined with a Group VIII metal described in U.S. Pat. No. 3,856,872, incorporated by reference as if set forth at length herein, are also useful in the present invention.

The zeolites described above can be composited with an inert binder such that the resulting composite catalyst particles are characterized by a combination of size, shape and density to be classified as Geldart Type A powders.

The use of a $CO_2$ laser as an electromagnetic radiation source has been reported for use in activating and cleaning oxide surfaces as mentioned above. However, the mentioned report gives no indication about the applicability of this technique for use in the preparation and characterization of zeolites, which have distinctly different chemical structures and absorption frequencies. Furthermore, the design of applicants' cell and optical train depart significantly from that reported.

A schematic of the overall configuration of the apparatus is shown in FIG. 1. The electromagnetic radiation source illustrated an 8 W, continuous-wave $CO_2$ laser (Melles Griot 05 COP 080) having an output at 10.6 m. The irradiance of the electromagnetic radiation at the sample is at least 2 watts per square centimeter. Commercially available infrared lasers such as Nd:YAG or HF lasers can also be used. Beam diameter is 1.6 mm with a full angle divergence of less that 6.5 mrad; beam mode structure is transverse electromagnetic $TEM_{oo}$. For a mathematical description of such laser output, see O'Shea, *An Introduction To Lasers and Their Applications*, pp. 94–97, Addison Wesley (1977); Yariv, *Introduction to Optical Electronics*, pp. 39–43; Rinehart and Winston (1976), hereby incorporated by reference. The linearly polarized output beam of the laser passes through a variable polarization analyzer (VPA) (California Laser Corp.) which permits continuous control of laser power from 0 to 8 W. The beam then passes through a beam splitter, which is optional to provide a signal to a power meter (Scientech 36-0001) for continuous monitoring of power level stability. The beam then passes through a beam expander (Two-Six, Inc.) to expand the beam as desired to uniformly irradiate the catalyst sample wafer in the IR cell at an irradiance of at least 2 watts/cm$^2$. By adjusting the laser power and duration of irradiation, the temperature of the sample may be regulated. Of course, the binder for the sample may also be thermally treated by this method.

Sample temperatures are monitored by a fine wire thermocouple and/or optical pyrometry, which measures temperature based on the thermal emission from the heated sample. The fine wire thermocouple can also be used to support the sample. All window and lens elements in the design are ZnSe to prevent problems associated with salt windows, in particular moisture sensitivity. The laser, VPA, beam splitter, and beam expander are all mounted on an optical rail which is attached to the FTIR and co-axially aligned with the sample IR cell.

Figure 4:
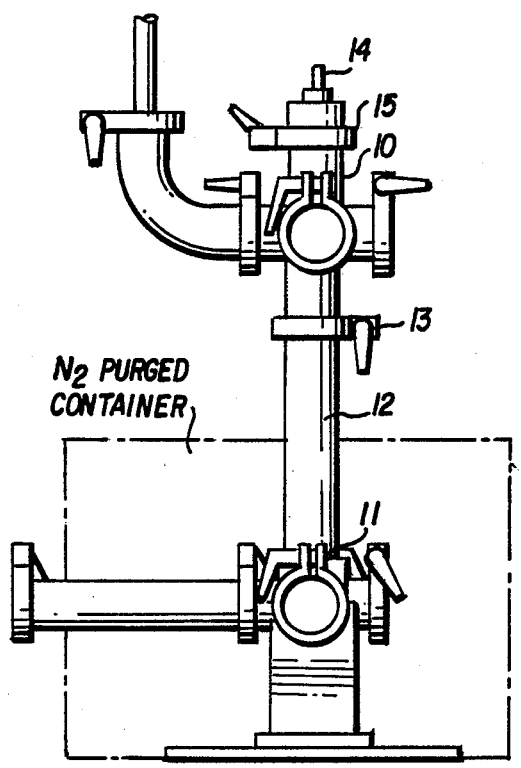
FIG. 4 shows a front view of the cell.

The cell comprises two stacked stainless steel crosses 10, 11 (1.5 in. O.D.) connected via stainless steel vacuum flanges. See FIG. 4. The crosses comprise intersecting conduits. The laser cross 11 provides optical access for the $CO_2$ laser beam along one horizontal axis. Optical access for an analyzer is also gained via the lower cross. These accesses are preferably tubular. Their longitudinal axes are disposed in the same plane and preferably are perpendicular to each other. The laser cross is housed in an enclosure as designated by the dashed line in FIG. 4. Any conventional enclosure can be used which seals the environment of the laser cross so that it can be purged with nitrogen or other inert gas. The access for the laser may project beyond the enclosure. The access for the analyzer (not shown) does not.

The stacked crosses are connected by a conduit 12 whose longitudinal axis intersects the intersection of the longitudinal axes of the accesses. Simply they are the x, y, z axes of a cartesian coordinate system. Conduit 12 protrudes from the enclosure and is connected to cross 10 by a conventional vacuum fitting 13. Attached to cross 10 and positioned co-axially with conduit 12 is rotary/linear motion feedthrough 14, which is attached to cross 10 via a quick-disconnect vacuum flange fitting 15.

Figure 5:
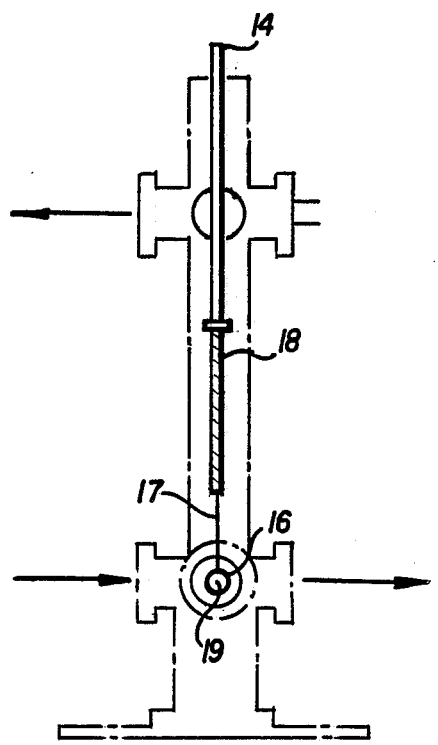
FIG. 5 shows in section a side view of the cell depicting the sample holder.

The uppermost cross 10 has accesses for a vacuum source and pyrometer. Those things are not shown. The disposition of those accesses is a matter of convenience. A low-mass sample holder or support is attached to the rotary/linear motion feedthrough 14 conduit. The holder can rotate or be moved along the longitudinal axis of the conduit 12. Of course, it is removable from the cell. The holder comprises an approximately 1.5 cm diameter double loop 16 of fine nichrome wire 17 positioned at the intersection of the longitudinal axes of the conduits of cross 11. See FIG. 5. This is a substantially negligible mass preferably weighing between 0.01 g and 0.8 g. The loop 16 is attached via nichrome leads to an alumina tube 18, which is mounted preferably coaxially on the longitudinal axis of the rotary/linear motion feedthrough 14 which extends co-axially inside conduit 12. The loop holds the sample wafer 19 and insures minimal heat loss by conduction. The size of the sample wafer is conventional. When the loop is rotated perpendicular to the laser beam, a background FTIR spectrum can be taken; and the sample is heated. Immediately after heating, the sample is rotated, preferably 90 degrees, into the FTIR beam to take its spectrum. Of course, either the holder or cell may be rotated. However, if the cell is rotated, plural intersecting conduits of cross 11 are unnecessary.

Typically, the cell is mounted in the FTIR sample compartment such that a continuous $N_2$ purge is maintained around the cell, even when changing samples. Thus, the subject construction permits sample removal without requiring optical realignment or breaking the nitrogen envelope of the cell compartment within the spectrometer. This permits spectra acquisition without interfering bands from air entering the sample cell compartment. Such interference problems plagues prior art designs and methods. For example, atmospheric $CO_2$ interference was noted in the prior work by Abbate and appears clearly in FIG. 4 of that reference.

In operation of the present invention, the sample is loaded into the cell. It is evacuated. A background spectrum is taken. The sample is continuously irradiated. It is rotated. A spectrum of the irradiated sample is taken. The sample is unloaded from the cell. The activation and analysis are essentially simultaneous, that is, occur in rapid, continuous succession without disassembly of the cell. Thus the integrity of the cell is maintained throughout the continuous process. Also, rapid cool down allows several sequential tests for full sample treatment, such as desorption, without long cool down times normally required for conventional thermal cells.

In operation according to the prior art, an empty cell is evacuated. A background spectrum is taken. The cell is disassembled and the purge of the cell environment is broken. Then the cell is loaded with a sample and evacuated. The sample is irradiated. A sample spectrum is taken. To unload the sample, the cell is disassembled and the purge of the cell environment is broken. This discontinuous process points out advantages of applicants' process and apparatus.

This invention can also be used for binder activation, high temperature solid state ion exchange, phase transition studies, etc. For binder activation, see generally, U.S. Pat. No. 4,559,314 and Shibabi, Aluminum Insertion into High Silica Zeolite Frameworks, J. Catalysis 93,471 (1985), hereby incorporated by reference. Overall, the invention relates to any high temperature process which normally requires extensive sample calcination or high temperature treatment.

Although the example below uses a continuous wave laser, a pulsed laser works as well and provides even more controlled heat-up/cool-down cycles. This attribute makes pulsed lasers attractive for the case where the Electromagnetically Induced Thermal Desorption (EITD) apparatus is used as a novel type of pulse reactor for carrying out reactions over catalysts in two different modes of operation. In conventional pulse reactors, the catalyst is maintained at a constant temperature while the reactant(s) is pulsed over it. Using the current apparatus with a pulsed source of electromagnetic radiation permits more precise control of sample temperature than conventional pulse reactors, maintaining it at a constant level by essentially instantaneously balancing heat gain and heat loss through proper choice of pulse power and repetition rate. Here, in a constant temperature mode of operation, the resultant product distribution is governed by transient, non-equilibrium sorption/desorption events. In contrast, the EITD apparatus is also used as a pulse reactor in a completely different mode. In this case, a steady state, equilibrium sorption of reactant(s) is first achieved, followed by a rapid (quasi-instantaneous) pulse of catalyst heating, caused by a pulse of electromagnetic irradiation from a source of electromagnetic radiation. In this case, the temperature is pulsed, not the reactant(s).

EXAMPLE

The invention will now be described with respect to experimentation which is considered non-limiting.

Figure 2A:
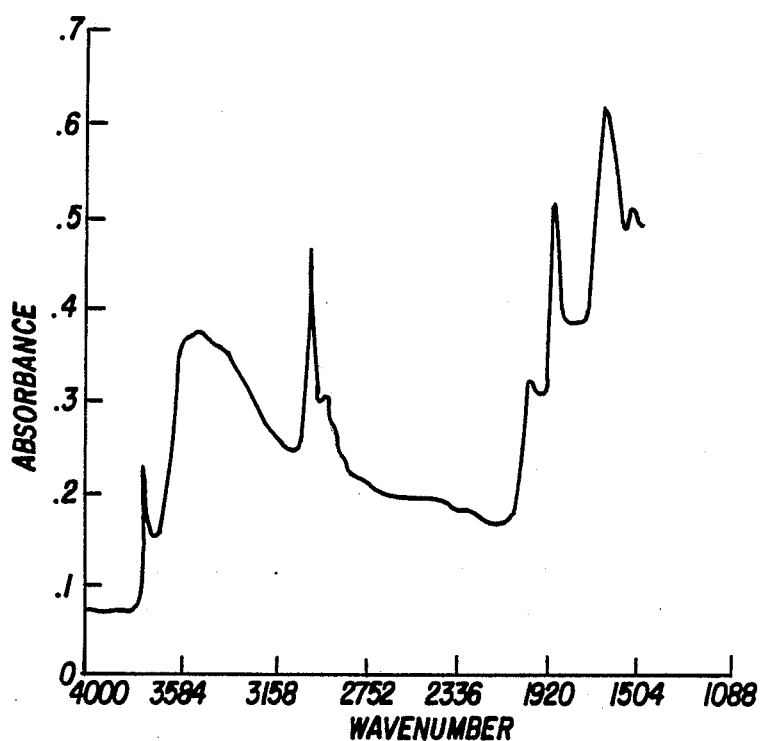
FIG. 2(*a*), (*b*), and (*c*) depict the results of experimentation upon a ZSM-5 zeolite type catalysts before desorption, after full desorption using the method and apparatus of the present invention, and after full desorption using a conventional thermal cell.

Initial Sample Condition:

A 17 mg sample of 70:1 HZSM-5 sieved to <150μm is pressed into a wafer with a 1 in. diameter die at 10,000 to 20,000 lbs., and the sample is loaded into the sample holder. The sample holder is inserted into the sample cell, and the cell evacuated to $1 \times 10^{-5}$ torr. After taking a background spectrum, the initial spectrum of the sample prior to heat treatment is recorded and is shown in FIG. 2(a). Note the broad peak due to $H_2O$ at about 3400 $cm^{-1}$, which obscures the —OH stretch associated with framework Al. Some hydrocarbon impurity sorbed on the zeolite is also evident at about 2950 $cm^{-1}$.

Figure 2B:
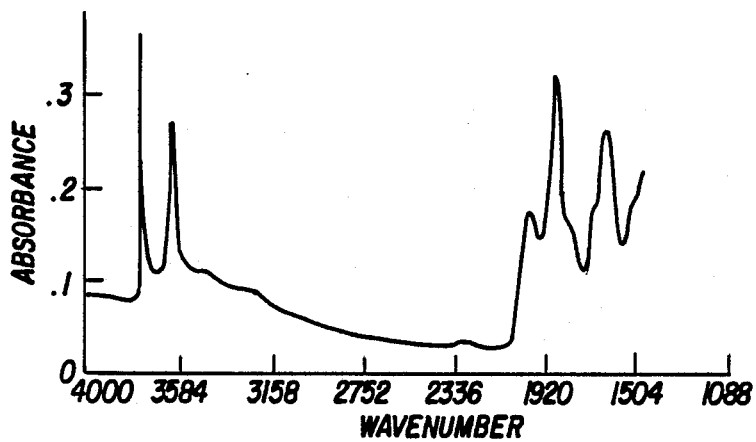
Figure 2C:
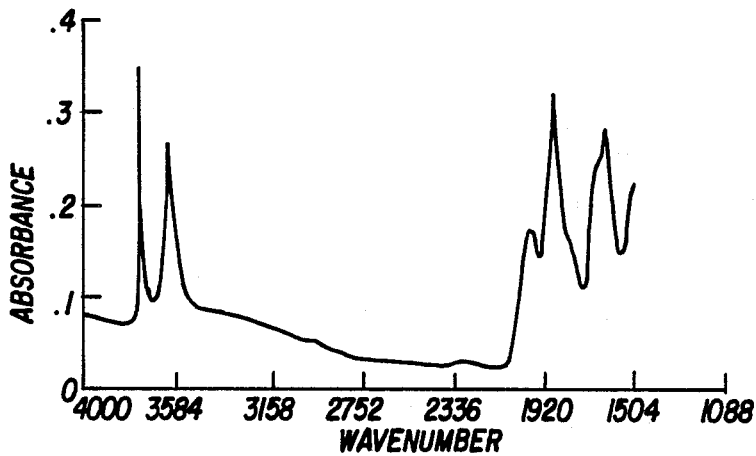

Desorption:

After exposure to laser power of 2 W for 30 seconds, the sample is fully desorbed, as shown in FIG. 2(b), a spectrum which is taken about 1 minute after turning the laser power off. The Al—OH peak at 3610 $cm^{-1}$ is clearly evident, unencumbered by the complicating $H_2O$ background. The hydrocarbon impurity at about 2950 $cm^{-1}$ is also absent. Absorbance due to $H_2O$ in the region below $cm^{-1}$ is also eliminated. For comparison, FIG. 2(c) shows a sample of this zeolite which is calcined using a conventional thermal cell furnace as follows: temperature ramped from R.T. to 450° C. at 3° C./minute, hold for 1 hour at 450° C. The spectrum in FIG. 2(c) is obtained after an additional period of 3 hours to permit for sample cool-down. The current technique accomplished desorption at an effective temperature of 450° C. and permitted a spectrum to be taken, all within a period of 2 minutes.

Dehydroxylation:

After further exposure for 30 seconds at 4 W, dehydroxylation of the zeolite occurs, as evidenced by the decrease in the 3610 $cm^{-1}$ peak, as shown in FIG. 3(a). FIG. 3(b) shows the spectrum of the sample before dehydroxylation (FIG. 2(c) recast to the same scale as FIG. 3(a)). Further dehydroxylation is achieved upon additional laser exposure.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

We claim:

1. A method for selectively thermally treating samples comprising essentially instantaneously activating a sample exclusively using a beam of electromagnetic radiation having a wavelength between about 0.1 μm and 100μm and an energy distribution given by transverse electromagnetic mode $TEM_{oo}$ and analyzing the selectively thermally treated sample.

2. The method according to claim 1, wherein the wavelength distribution is between about 1 μm and 20 μm.

3. The method according to claim 1, wherein the sample is a catalyst.

4. The method according to claim 3, wherein the catalyst is a zeolite.

5. The method according to claim 4, wherein the zeolite is a ZSM-5 zeolite, alpha zeolite, APO zeolite or layered silicate.

6. The method according to claim 1, wherein the beam of electromagnetic radiation is obtained from a laser.

7. The method according to claim 6, wherein the laser is a $CO_2$, Nd:YAG or HF laser.

8. The method according to claim 3, wherein the activation is dehydroxylation.

9. The method according to claim 3, wherein the activation is desorption.

10. The method according to claim 3, wherein the activation is dealumination.

11. The method according to claim 1, wherein the beam of electromagnetic radiation is processed through a variable polarization analyzer, beam splitter and beam expander prior to irradiation of the sample supported in a cell under vacuum.

12. The method according to claim 1, wherein the sample being irradiated in a cell is monitored by an infrared analyzer.

13. The method according to claim 1, wherein the sample being irradiated is supported using a negligible mass holder in a vacuum cell.

14. The method according to claim 13, wherein the sample is supported by a wire.

15. The method according to claim 14, wherein the wire is nichrome wire.

16. The method according to claim 1, wherein the sample includes a binder.

17. The method according to claim 1, wherein the irradiance of the electromagnetic radiation at the sample is at least 2 watts per square centimeter.

18. The method according to claim 1, wherein substantially only the framework of the sample absorbs energy of the electromagnetic radiation.

19. The method according to claim 1, wherein the process is continuous and activation occurs from about 0.5 to 3 minutes.

20. The method according to claim 1, wherein the activation and analysis are essentially simultaneous.

21. A cell for thermally activating and analyzing samples comprising a sample holder having a substantially negligible mass to support a sample, the cell is constructed and arranged so that a beam from an electromagnetic radiation means exclusively heats the sample supported by the sample holder and so that the irradiated sample can also be analyzed essentially simultaneously.

22. The cell according to claim 21, wherein the electromagnetic radiation is processed through a variable polarization analyzer.

23. The cell according to claim 22, wherein the electromagnetic radiation is further processed through a beam splitter.

24. The cell according to claim 22, wherein the electromagnetic power of the electromagnetic radiation is monitored.

25. The cell according to claim 23, wherein the electromagnetic radiation passes through a beam expander.

26. The cell according to claim 21, wherein the sample is supported by a wire loop in the cell.

27. The cell according to claim 26, wherein the wire is a nichrome wire.

28. The cell according to claim 26, wherein the wire loop is a thermocouple.

29. The cell according to claim 21, wherein the cell is a vacuum cell.

30. The cell according to claim 21, wherein the temperature of the sample is monitored by an IR pyrometer or thermocouple.

31. The cell according to claim 21, wherein the sample is monitored by an IR analyzer.

32. The cell according to claim 21, wherein the electromagnetic radiation has an energy distribution given by transverse electromagnetic mode $TEM_{oo}$.

33. The cell according to claim 21, wherein the electromagnetic radiation means is a laser.

34. The cell according to claim 33, wherein the laser is an infrared laser.

35. The cell according to claim 34, wherein the laser is a $CO_2$, Nd:YAG or HF laser.

36. The cell according to claim 21, wherein sample activation is desorption, dehydroxylation or dealumination.

37. The cell according to claim 21, wherein the sample is a catalyst.

38. The cell according to claim 37, wherein the catalyst is a zeolite.

39. The cell according to claim 21, wherein the sample includes a binder.

40. The cell according to claim 38, wherein the zeolite is a ZSM-5 zeolite, alpha zeolite, APO zeolite or layered silicate.

41. The cell according to claim 21, wherein irradiance of the electromagnetic radiation at the sample is at least 2 watts per square centimeter.

42. The cell according to claim 21, wherein substantially only the framework of the sample absorbs energy of the electromagnetic radiation.

43. The cell according to claim 21, wherein the cell comprises three conduits which cross or intersect each other.

44. The cell according to claim 43, wherein the longitudinal axis of two of the conduits lie in the same plane.

45. The cell according to claim 44, wherein the longitudinal axes of the two conduits intersect at a right angle.

46. The cell according to claim 45, wherein the third conduit has a longitudinal axis which intersects the plane at the intersection of axes of the two conduits at a right angle.

47. The cell according to claim 43, wherein the conduits are tubular having ZnSe windows sealing their distal ends.

48. The cell according to claim 43, wherein the cell is sealed in an enclosure.

49. The cell according to claim 46, further comprising additional conduits having longitudinal axes intersecting the longitudinal axis of the third conduit.

50. The cell according to claim 49, wherein one of the additional conduits has a vacuum connection.

51. The cell according to claim 21, wherein the sample holder rotates.

52. The cell according to claim 43, wherein the longitudinal axis of the sample holder is parallel to the longitudinal axis of one of the conduits.

53. A cell for thermally activating and analyzing samples comprising at least three conduits, two of the conduits having longitudinal axes which intersect in one plane, the third conduit having a longitudinal axis which intersects the intersection of the axes of the two conduits, these two conduits being sealed at their distal end by laser and analyzer visible windows, a rotatable sample holder comprising a fine wire holder is located in the cell, the sample holder has a longitudinal axis parallel to that of the third conduit, the distal ends of the third conduit are sealed.

54. An apparatus for thermally activating and analyzing samples comprising a source for a beam of electromagnetic radiation, a variable polarization analyzer, beam splitter, and beam expander for processing the electromagnetic radiation which then irradiates a sample supported in a cell sealed in an enclosure which cell is constructed and arranged so that the electromagnetic radiation exclusively heats the sample supported by a sample holder in the cell and so that the irradiated sample can also be analyzed essentially simultaneously.

* * * * *